(12) United States Patent
Morrison

(10) Patent No.: US 8,446,156 B2
(45) Date of Patent: May 21, 2013

(54) ROCK ANALYSIS APPARATUS AND METHOD

(75) Inventor: Robert D. Morrison, Brookfield (AU)

(73) Assignee: The University of Queensland, Brisbane (AU)

( * ) Notice: Subject to any disclaimer, the term of this patent is extended or adjusted under 35 U.S.C. 154(b) by 707 days.

(21) Appl. No.: 12/377,130

(22) PCT Filed: Aug. 10, 2007

(86) PCT No.: PCT/AU2007/001120
§ 371 (c)(1),
(2), (4) Date: Apr. 14, 2010

(87) PCT Pub. No.: WO2008/017120
PCT Pub. Date: Feb. 14, 2008

(65) Prior Publication Data
US 2010/0204825 A1     Aug. 12, 2010

(30) Foreign Application Priority Data
Aug. 11, 2006   (AU) ................................ 2006904353

(51) Int. Cl.
*G01R 27/04* (2006.01)
(52) U.S. Cl.
USPC ........... 324/637; 324/344; 324/250; 324/368; 324/336; 209/3.1; 209/539; 209/576
(58) Field of Classification Search
USPC .. 324/250, 637–646, 336, 362, 344; 374/129, 374/122, 120, 4, 5, 7, 45, 47; 209/3.1, 539, 209/576
See application file for complete search history.

(56) References Cited

U.S. PATENT DOCUMENTS

| | | | |
|---|---|---|---|
| 4,933,075 A * | 6/1990 | Nordin et al. ................. | 209/576 |
| 4,996,421 A | 2/1991 | Rai et al. | |

(Continued)

FOREIGN PATENT DOCUMENTS

| | | |
|---|---|---|
| AU | 2000/35312 | 11/2000 |
| CN | 1668769 A | 9/2005 |

(Continued)

OTHER PUBLICATIONS

Derwent Abstract Accession No. 88-056701/08, ZA 8 702 406 A (ORE SORTERS SA PTY) Sep. 24, 1987.

(Continued)

*Primary Examiner* — Jermele M Hollington
*Assistant Examiner* — Son Le
(74) *Attorney, Agent, or Firm* — Edwards Wildman Palmer LLP; Peter F. Corless; Lisa Swiszcz

(57) ABSTRACT

The invention provides a method and apparatus for the analysis of rocks and rock fragments. A method for the analysis of a rock fragment including: feeding the rock fragment to a microwave irradiation zone of microwave energy generated by a microwave source; gauging energy absorbed by the rock fragment; and correlating rate of change of the gauged energy absorbed by the rock fragment with compositional characteristics of the rock fragment. The rock fragment analysis assembly including: a microwave energy source that generates a microwave irradiation zone; a rock fragment feed that facilitates the feeding of rock fragments into the microwave irradiation zone; at least one primary sensor located on a microwave energy source side of the microwave irradiation zone for gauging microwave energy absorbed by the rock fragments in the microwave irradiation zone; and a processing unit for correlating rate of change of the gauged energy 26 absorbed by the rock fragments with compositional characteristics of the rock fragments.

19 Claims, 1 Drawing Sheet

U.S. PATENT DOCUMENTS

| | | | |
|---|---|---|---|
| 5,148,923 A * | 9/1992 | Fraenkel et al. | 209/539 |
| 5,209,355 A * | 5/1993 | Mindermann | 209/3.1 |
| 5,741,707 A | 4/1998 | Herron et al. | |
| 2006/0096415 A1 | 5/2006 | Batterham et al. | |

FOREIGN PATENT DOCUMENTS

| | | | |
|---|---|---|---|
| GB | 2004371 A | 3/1979 | |
| GB | 2 188 727 | 10/1987 | |
| GB | 2 198 242 | 6/1988 | |
| GB | 2206213 A | 12/1988 | |
| GB | 2211299 A * | 6/1989 | |
| GB | 2211299 A | 6/1989 | |
| GB | 2230099 A | 10/1990 | |
| WO | 01/37000 | 5/2001 | |
| WO | 03/072835 | 9/2003 | |
| WO | WO-2004/029600 A1 | 4/2004 | |
| WO | 2006/034553 | 4/2006 | |

OTHER PUBLICATIONS

Chinese Office Action dated Nov. 10, 2010, corresponding to Chinese Patent Application No. 200780029837.7.

Supplementary European Search Report for corresponding EP 07784760.6, Feb. 11, 2009.

* cited by examiner

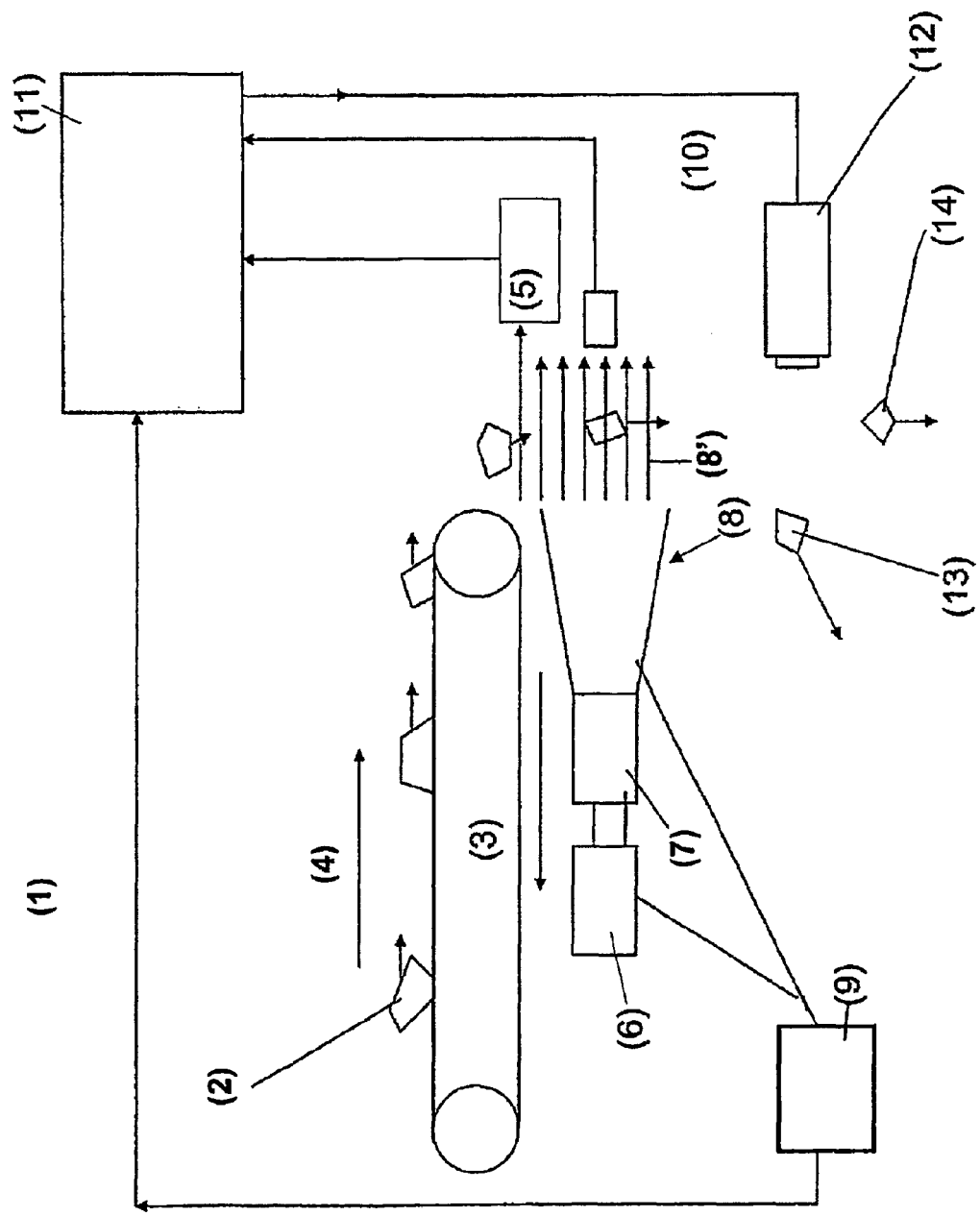

ROCK ANALYSIS APPARATUS AND METHOD

FIELD OF THE INVENTION

This invention relates to a rock analysis apparatus and method. This invention has particular but not exclusive application to assessing mineral content, and in particular cases mineral composition, within rock fragments, and for illustrative purposes reference will be made to such an application. However, it is to be understood that this invention could be used in other applications, such as assessing mineral content and/or distribution within rocks, in mining, in other geological contexts and in research.

BACKGROUND TO THE INVENTION

Rocks typically comprise an aggregate of minerals in varying concentrations and at least some water, either absorbed or chemically bound. Early methods of analysing fragmentary rock samples have included irradiating the samples with microwave radiation for a relatively long period of time, generally in the order of several seconds or more. The microwave radiation differentially heats the rock fragments as observed by, for example, thermal imaging such as by an infra-red imaging device. Different fragments and/or areas of fragments of the rock sample are composed of different minerals and/or water content, and as such these areas will each increase in temperature to a different degree in response to the microwave irradiation.

One currently favoured application under development employs the use of microwave energy to heat conductive minerals to either directly cause particle fragmentation or to weaken the particle for subsequent fragmentation, or to induce fluid pathways to enhance later processing.

The invention described herein proposes to measure the microwave energy absorbed by each particle or rock fragment at much lower levels of microwave irradiation and use this as the basis of rejection of barren particles end possible selection between high and low grade particles containing specific minerals. The primary detection method generally includes monitoring of the degree of coupling between a suitable microwave source and the target particle. A particle which has no dielectric coupling will probably have a very low content of conductive minerals or semi-conductors such as sulphides.

Further, as minerals which behave as semi-conductors are heated, their charge carriers become more mobile and the degree of coupling to a suitable source will increase. If the rock particle which is being irradiated contains only one semi-conductor species, it should display a characteristic rate of increase of coupling. This provides an opportunity to distinguish between semi-conductor minerals as well as to estimate their presence and content.

The primary detection method advantageously provides a very rapid response. Indeed, the heating/energy absorption process is virtually instantaneous. As such, any change in energy absorption can be detected immediately. Further, there is advantageously no need to wait for heating to occur. The proposed method is also complimentary with methods for the detection of mineral content by thermal imaging. The required elements of a sorting device for carrying out the method of the invention could therefore share a particle sorting device including thermal imaging means.

SUMMARY OF THE INVENTION

According to one aspect of the invention them is provided a method for the analysis of a rock fragment including:

feeding the rock fragment to a microwave irradiation zone of microwave energy generated by a microwave source; gauging energy absorbed by the rock fragment; and correlating rate of change of the gauged energy absorbed by the rock fragment with compositional characteristics of the rock fragment.

The rock fragment may be fed to the microwave irradiation zone by any suitable means. According to one embodiment, the rock fragment is fed to the microwave irradiation zone by a conveyer and allowed to drop through the microwave irradiation zone under the action of gravity.

In order to increase throughput of rock fragments, in a preferred embodiment a plurality of rock fragments are fed to the microwave irradiation zone in a fragment feed channel. More preferably, a plurality of rock fragments are fed to the microwave irradiation zone in a plurality of discrete fragment feed channels.

The present invention requires gauging of the energy absorbed by the rock fragment as it passes through the microwave irradiation zone. This feature will be dealt with in some detail below. However, the energy absorbed by the rock fragment is preferably gauged by at least one sensor located on a microwave source side of the microwave irradiation zone.

As will also be discussed in more detail below, the analysis of the rock fragment may be supplemented by also gauging the intensity of microwave energy on a non-microwave source side of the microwave irradiation zone, after the microwave energy has passed through the rock fragment. This is, however, an optional feature of the invention.

In order to supplement the analysis even further, the method may include the step of gauging the size of the rock fragment and the time period for which the rock fragment is in the microwave irradiation zone. The size and time period may be gauged by means of, for example, a visible light camera.

The correlation of the rate of change of the gauged energy absorbed by the rock fragment may be conducted using any suitable means. It will be appreciated that this is preferably conducted in real time. Therefore, it is preferred that the correlation be conducted using a data processing unit.

After the correlation of the rate of change of the gauged energy absorbed by the rock fragment with compositional characteristics of the rock fragment, the rock fragment may be directed for downstream processing or is discarded as desired. This may be based on the presence or absence of a particular mineral of interest, and/or may be based on quantity of a particular mineral in the fragment, for example whether the fragment is a high grade or low grade ore. In one embodiment the rock fragment is directed for downstream processing or is discarded using a high pressure air separator, a separating conveyer or other device.

According to another aspect of the invention there is provided a rock fragment analysis assembly including:
 a microwave energy source that generates a microwave irradiation zone;
 a rock fragment feed that facilitates the feeding of rock fragments into the microwave irradiation zone;
 at least one primary sensor for gauging microwave energy absorbed by the rock fragments in the microwave irradiation zone; and
 a processing unit for correlating rate of change of the gauged energy absorbed by the rock fragments with compositional characteristics of the rock fragments;
 wherein said at least one primary sensor is located on a microwave energy source side of the microwave irradiation zone The microwave energy source may include any suitable source as used in industry. For example, the microwave energy source may include an excitation source, a microwave generating cavity and a wave guide for generating the microwave irradiation zone.

As was the case with the method of the invention, the rock fragments may be fed to the microwave irradiation zone by any suitable means. The rock fragment feed may therefore take any suitable form. In a preferred embodiment the rock fragment feed includes a conveyer including a drive and a belt orientated to feed the rock fragments to a position directly above the microwave irradiation zone such that the rock fragments drop through the microwave irradiation zone under the action of gravity when the rock fragments leave the conveyer. The conveyer may include a plurality of discrete fragment feed channels to facilitate increased throughput of rock fragments. The primary sensor may take any suitable form. Preferably the primary sensor is constituted by an electrical circuit including a meter that is monitored by a fast analogue to digital converter and that is preferably synchronised with frequency peaks of the microwave source. The meter advantageously facilitates monitoring of current, voltage and phase shift in exciting power applied to the microwave irradiation zone.

Again, as was the case with the above described method, the correlation of the rate of change of the gauged energy absorption with compositional characteristics of the rock fragments is preferably conducted in real time. Therefore, it is preferred that the processing unit includes a computer unit including a library for correlating the rate of change of the gauged energy absorbed by the rock fragments with compositional characteristics of the rock fragments.

In order to provide supplemental analysis to that provided by the primary sensor or sensors, the assembly preferably includes a secondary sensor located on a non-microwave energy source side of the microwave irradiation zone for gauging the intensity of microwave energy after the microwave energy has passed through the rock fragment.

Likewise, in order to supplement the analysis of the primary sensor(s), the assembly may additionally include a tertiary sensor for gauging the size of the rock fragment and the time period for which the rock fragment is in the microwave irradiation zone. The tertiary sensor may be included whether or not the secondary sensor is included, and vice versa.

If included, the tertiary sensor may take any suitable form. Preferably the tertiary sensor is a visible light camera. The image obtained using the visible light camera may be used for a correction based on an estimate of particle mass if required.

Generally, the analysis of the rock fragment will take place in real time. As such, in a preferred embodiment the assembly includes a separator for separating rock fragments for downstream processing or for discarding. The separator is, in particular embodiments, a high pressure air separator or a separating conveyor.

The method of the invention may be used in conjunction with other methods of analysis. For example, the method of the invention may be used in conjunction with a thermal imaging method that includes inducing differential heating in the rock fragments through microwave irradiation, thermally imaging the fragments and analysing the resultant thermal image/s to determine the mineral content of each fragment by reference to its thermal signature. The present invention is also complimentary to methods which use high power levels with the objective of inducing fracture or breakage.

DETAILED DESCRIPTION OF THE INVENTION

Turning to the theory behind the invention, but not wanting to be necessarily bound thereto, the presence or absence of minerals of interest on the rock fragments will be detected based on the efficiency of absorption of energy from the pulsed (or continuous) microwave irradiation. This may be achieved by measuring the degree of coupling which occurs in the presence or absence of a particular type of target particle.

When minerals that behave as semi-conductors are heated the electrons or charge carriers of the minerals become more mobile and the degree of coupling to a suitable microwave source increases. If the rock fragment that is being irradiated contains only one semi-conductor species, it should display a characteristic rate of increase of coupling. This provides an opportunity to distinguish between semi-conductor minerals as well as to estimate their presence and content.

In the null case, where there are no semi-conductive minerals present or any other minerals which absorb energy when irradiated with microwaves, the degree of coupling will be negligible.

In the case where non semi-conductor minerals which absorb energy when irradiated with microwaves are present, the response with heating should be close to linear and the degree of coupling will remain the same as the mineral is heated.

In the case where a semi-conductor mineral is present, all of which will absorb energy when irradiated with microwaves, the degree of coupling to a suitable source will increase and that increase will depend on the absolute temperature of the mineral in a systematic way.

The following equation will govern this behaviour:

$$n_e = \alpha * \exp[-E/2KT]$$

where:
$n_e$ is the number of conduction electrons per unit volume;
a is a constant of proportionality;
E is the activation energy to transfer an electron from one atom to the next;
K is Boltzman's constant; and
T is the absolute temperature in kelvin.

Nernst equivalent equation (after the Practical Handbook of Physical Properties of Rocks and Minerals Published CRC p 363)

The effective conductivity of a mineral should be directly proportional to the number of available electrons or carriers. Hence, as the temperature increases, the conductivity will also increase. For example, if the typical ambient temperature is 300 kelvin, increasing mineral temperature by 30 kelvin (to approx 60° C.) will reduce the resistance by 10%. Hence, relatively small increases in temperature will cause a rapid increase in conductivity.

Most mineral sulfides exhibit zero frequency resistivity (ohm/m) of $1-10\times10^{-6}$. However, pyrite which is a major gangue sulphide, and a source of acid mine drainage, has a resistivity of $1-600\times10^{-3}$. This will therefore be much more susceptible to heating and rapid decrease in resistivity.

There is substantial variation in mineral resistivity and frequency response between different sources because impurities make an important contribution to semi-conductivity. Hence, the proposed method will preferably be tested and optimised for different ore deposits.

In the case of a mixture of semi-conductor minerals, the degree of coupling to a suitable source will increase, as described above, but in a manner which represents the combined degrees of coupling and heating of the minerals present. The behaviour will be dominated by a balance between the mineral that is present in the highest concentration and the mineral that is the most conductive. The presence of semi-conductive minerals will be apparent, but only a very approximate guide to the type or concentration of the minerals will be provided.

The present invention is distinguished from other microwave intensive methods that can be used to induce microfractures in rock fragments to lessen the subsequent crushing required. The power density of the microwave irradiation used for this practice is generally in the range of $10^9$ to $10^{11}$ $W/m^3$.

The method of the invention is also distinguished from the use of pulsed microwave radiation of low power density in the analysis of fragmentary samples to determine the abundance of microwave-absorbing minerals by virtue of their dielectric coefficients. This is usually measured by sensing the change in the resonant frequency caused by the presence of the sample within the resonant cavity.

In the case of the method of the invention it is not necessary to induce a thermal shock into the system to weaken the rock, but it is necessary to induce sufficient heating for the increase in charge carrier mobility to be detectable.

It will be appreciated that either dry feed materials should be used in the method of the invention, or microwave frequencies selected that avoid strong interaction with any water present.

Different semi-conductor minerals will also respond differently to microwave length/frequency. There is, therefore, a potential to maximise sensitivity to the mineral of most interest when employing the method of the invention.

The method of the invention may advantageously facilitate not only the Identification of fragments containing minerals within a population of fragments, but also quantification of the mineral content. The relative changes caused by differential absorption of energy will also be enhanced by the use of a lower power microwave source, be that pulsed or continuous.

In a preferred embodiment pulsed microwave irradiation is applied at a power density below $10^9$ $W/m^3$, more preferably in a range of from $10^7$ and $10^9$ $W/m^3$.

If pulsed microwave energy is employed, the energy absorbed during each pulse will increase in ratio with the quantity (and electrical continuity) of mineral present in the irradiation zone. As such, if three or four pulses are applied in quick succession, the slope of a graph of power versus pulse number should be indicative of, or correlate with, the mineral or mixture of minerals present in the irradiation zone.

As the heating process is very rapid, a plot of energy absorbed versus time should also give a characteristic curve which depends on the mineral or minerals present in the microwave irradiation zone. If there are no semi-conductors present, some energy may be absorbed but the amount will not increase to any great extent with temperature, providing a second criterion for rejection.

In both cases, the absolute quantity of energy absorbed will be a guide to the absolute quantity of mineral present, assuming the texture (i.e. physical arrangement) of the mineral is reasonably consistent. If some measure of particle size and mass is provided, these may be combined to estimate a mineral grade. That is, the proportion of the mineral that is present.

In one embodiment, as described briefly above, rock fragments are fed to the microwave irradiation zone in a channel. Each channel, or rock fragment path, is provided with a dedicated microwave source. The energy drawn from the source during one or more pulses may be measured and used as the basis of an estimate of conductive mineral composition within the target fragment. This detection method will advantageously provide a rapid response.

In an alternative embodiment, each channel or rock fragment path is provided with a dedicated continuous microwave source. The energy drawn from the source as the fragment(s) passes through the irradiation zone may be measured at several short time intervals and used as the basis of an estimate of conductive mineral composition within the target fragment. This detection method will also advantageously provide a rapid response.

As previously noted, a supplementary sensor or detector may be placed on a side of the irradiation zone that is opposite that of the microwave source. In that case, the sensor or detector is position in the microwave beam after it has passed through the rock fragment. In this embodiment, the remnant signal strength is monitored and related to the conductive mineral composition within the particle. If the energy level detected is similar to the signal strength detected with no particle present, then the particle is unlikely to contain any conductive grains.

In another embodiment the microwave frequency may be selected to minimise the absorption of energy by any surface moisture and/or absorbed moisture within the fragment, thereby maximising the absorption differential between the microwave absorbing minerals and other material. The frequency will generally be in the range of from 900 to 5800 MHz. Preferably the frequency is in the range of from 900 to 3500 MHZ, more preferably in the range of from 915 to 2450 MHz, even more preferably from 915 to 950 MHz.

Similarly the microwave pulse duration may be selected to minimise the heating/absorption of any surface moisture and/or absorbed moisture within the fragment, thereby maximising the absorption differential between the microwave absorbing minerals and other material.

It should be noted that any one or all of the steps described above may be automated. As previously described, it is preferred that the method provide real time analysis of the rock fragments. Therefore, it would be preferably if the entire process were automated.

DETAILED DESCRIPTION OF THE DRAWING

It will be convenient to hereinafter provide a detailed description of one embodiment of the invention with reference to the accompanying drawing. The purpose of providing this detailed description is to instruct persons having an interest in the subject matter of the invention how to put the invention into practice. It is to be clearly understood however that the specific nature of this detailed description does not supersede the generality of the preceding statements.

FIG. 1 depicts an assembly (1) in accordance with one embodiment of the present invention. Rock fragments (2) are transported by a conveyor (3) which is divided into one or more "channels" (4). Each channel is a single rock carrying path which allows each fragment to be separately presented to a source of microwave irradiation which is dedicated to that channel (4). Only one channel is shown in FIG. 1 for clarity.

Each channel (4) is provided with a detector (5) which identifies the leading and trailing edges of each fragment (2) and relays a signal to the computer. This might be a standard digital video camera supported by suitable image analysis software or a light (or laser) beam which is interrupted by the passage of each rock fragment. There are many possible implementations which would be suitable.

The assembly (1) includes an excitation source (6), a microwave generating resonant cavity (7), a wave guide (8), power detection sensors (9) and an optional transmission detector (10). An accessible zone of intense microwave activity (8') is generated at the end of the wave guide (8).

In the depicted embodiment the rock fragments (2) fall vertically through the microwave irradiation zone (8'). However, the fragments (2) may pass through the zone (8') in any direction. Falling vertically may be advantageous as it increases the likelihood of even distribution of the irradiation as the fragments tumble through the zone (8'). Similarly rock fragments must pass through the chamber individually.

Within the microwave irradiation zone (8) the rock fragments (2) are exposed to short pulsed or continuous microwave illumination of a selected frequency and intensity. The frequency is generally in the range of from 900 to 5800 MHz, although the frequency will be quite variable depending on the mineral or grade of interest. The pulsed microwave irradiation is generally applied at a power density below that which is required to induce micro-fractures in the rock fragments as described above.

As the fragments pass through the microwave zone (8'), the power absorbed from the microwave source by the interaction of the fragments with the microwave field is measured using sensors (9). The intensity of the microwave signal may optionally be measured after it passes through the fragment (2) by the transmission detector (10), but this will only be useful in the case where the fragment contains no minerals which absorb microwaves.

A wide range of electrical measurement techniques may be used to carry out either task. Predominantly high speed, digital circuit techniques are preferred for convenience of interfacing with a computer for rapid sorting decisions and actuation of the sorting mechanism. However, some analog implementations may also be practical.

One or more visible light cameras may be used to capture visible light images to allow determination of fragment size and the time at which a fragment of interest enters the irradiation zone and departs from it. This estimation may be supported and/or more mineral content may be quantified by comparison of the data with previously established microwave induced absorption properties of specifically graded and sized rock fragments.

The signals obtained as outlined above are sent to a data processing device (11) which will usually be a computer. The device (11) will identify each particle and calculate the time response to microwave irradiation for each of the cases described earlier. Based on the time response, an estimate of mineral type and content may be provided as criteria for the separation process.

Based on the content analysis individual rock fragments (2) may then be separated using a separator (12). Any appropriate conventional device may be used including a high pressure air separator that blows individual rock fragments in a particular direction to be further processed or discarded. The separator (12) separates the individual rock fragments (2) based on information sent by the processing device (11). The individual rock fragments (2) may be separated on the basis of, for example, estimated conductive mineral grade (or lack thereof), within the rock fragments.

In the apparatus depicted in FIG. 1, the separator (12) is a high pressure air separator that receives signals from the processing device (11). For example, the separator (12) may receive a signal to release high pressure air at the moment a rock fragment containing a high mineral content (13) passes it such that that fragment is directed to a specific collector. Low grade or gangue particles (14) are allowed to continue their free fall into a separate collector.

In this particular embodiment, for ease of understanding, the fragments have only been divided into two groups. However, it should be realized that this apparatus and method may be configured so that it is capable of separating the rock fragments across a scale of mineral content. In such a configuration if the separator (12) were a high pressure air separator, as in the current embodiment, it may blow air at varying force and/or direction, or multiple blowers may be used, for example for each fragment grade, to direct specific fragments to specific collectors dependent upon the level of mineral content or distribution pattern of the mineral within the rock.

Alternatively, or in combination, separate conveyer belts may direct the rock fragments to separate collectors.

In conclusion, the rock analysis apparatus and method of the invention may advantageously provide for separation of rock fragments on a number of criteria as follows:

1. If there is negligible energy change at sensors (9), and optionally sensor (10) no mineral is present;
2. If the energy drawn at sensors (9) does not increase with time, no mineral of interest is present;
3. If the energy drawn at sensors (9) does increase with time, the grade of the ore may be estimated using data obtained from the sensor or detector (5) that estimates fragment size and/or mass. The fragment may then be discarded if estimated to be under a desired ore grade;
4. If the energy drawn at sensors (9) does increase with time, it may be that the signature obtained suggests that a deleterious mineral is also present in the rock fragment. The fragment may then be discarded or separated for special downstream treatment; and
5. If the energy drawn at sensors (9) does increase with time, the target mineral may be present in sufficient grade to justify further processing.

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. A method for the analysis of a rock fragment including:
   feeding the rock fragment to a microwave irradiation zone of microwave energy generated by a microwave source;
   gauging energy absorbed by the rock fragment by measuring the degree of coupling to the microwave source; and
   correlating rate of change of the gauged energy absorbed by the rock fragment with compositional characteristics of the rock fragment,
   wherein the energy absorbed by the rock fragment is gauged by at least one sensor located on a microwave source side of the microwave irradiation zone;
   wherein said at least one sensor is constituted by an electrical circuit including a meter that is monitored by a fast analogue to digital converter;
   wherein said at least one sensor is synchronized with frequency peaks of the microwave source.

2. A method according to claim 1, wherein the rock fragment is fed to the microwave irradiation zone by a conveyer and allowed to drop through the microwave irradiation zone under the action of gravity.

3. A method according to claim 2, wherein a plurality of rock fragments are fed to the microwave irradiation zone in a fragment feed channel.

4. A method according to claim 2, wherein a plurality of rock fragments are fed to the microwave irradiation zone in a plurality of discrete fragment feed channels.

5. A method according to claim 1, including gauging the intensity of microwave energy on a non-microwave source side of the microwave irradiation zone, after the microwave energy has passed through the rock fragment.

6. A method according to claim 1, including gauging the size of the rock fragment and the time period for which the rock fragment is in the microwave irradiation zone.

7. A method according to claim 6, wherein the size and time period are gauged by means of a visible light camera.

8. A method according to claim 1, wherein the correlation of rate of change of the gauged energy absorbed by the rock fragment is conducted using a data processing unit.

9. A method according to claim 1, wherein after the correlation of rate of change of the gauged energy absorbed by the rock fragment with compositional characteristics of the rock fragment, the rock fragment is directed for downstream processing or is discarded.

10. A method according to claim 9, wherein the rock fragment is directed for downstream processing or is discarded using a high pressure air separator.

11. A rock fragment analysis assembly including:
- a microwave energy source that generates a microwave irradiation zone;
- a rock fragment feed that facilitates the feeding of rock fragments into the microwave irradiation zone;
- at least one primary sensor located on a microwave energy source side of the microwave irradiation zone for gauging microwave energy absorbed by the rock fragments in the microwave irradiation zone by measuring the degree of coupling to the microwave energy source;
- wherein said at least one primary sensor is constituted by an electrical circuit including a meter that is monitored by a fast analogue to digital converter;
- wherein said at least one primary sensor is synchronized with frequency peaks of the microwave source; and
- a processing unit for correlating rate of change of the gauged energy absorbed by the rock fragments with compositional characteristics of the rock fragments.

12. An assembly according to claim 11, wherein the microwave energy source includes an excitation source, a microwave generating cavity and a wave guide for generating the microwave irradiation zone.

13. An assembly according to claim 11, wherein the rock fragment feed includes a conveyer including a drive and a belt orientated to feed the rock fragments to a position directly above the microwave irradiation zone such that the rock fragments drop through the microwave irradiation zone under the action of gravity when the rock fragments leave the conveyer.

14. An assembly according to claim 11, wherein the processing unit includes a computer unit including a library for correlating rate of change of the gauged energy absorbed by the rock fragments with compositional characteristics of the rock fragments.

15. An assembly according to claim 11, including a secondary sensor located on a non-microwave energy source side of the microwave irradiation zone for gauging the intensity of microwave energy after the microwave energy has passed through the rock fragment.

16. An assembly according to claim 15, including a tertiary sensor for gauging the size of the rock fragment and the time period for which the rock fragment is in the microwave irradiation zone.

17. An assembly according to claim 16, wherein the tertiary sensor is a visible light camera.

18. An assembly according to claim 11, including a separator for separating rock fragments for downstream processing or for discarding.

19. An assembly according to claim 18, wherein the separator is a high pressure air separator.

* * * * *